United States Patent [19]

Beard

[11] Patent Number: 5,609,163

[45] Date of Patent: Mar. 11, 1997

[54] SURGICAL SHIELD FOR ORTHOPEDIC SURGERY

[76] Inventor: David M. Beard, 579 S. Willard St. Apartment 2, Burlington, Vt. 05401-4024

[21] Appl. No.: 578,858

[22] Filed: Dec. 27, 1995

[51] Int. Cl.$^6$ .................................................. A61F 5/37
[52] U.S. Cl. ........................................ 128/846; 128/847
[58] Field of Search ................................ 128/845, 846, 128/847, 849, 878, 879, 882; 5/604; 4/480, 482; 2/2

[56] References Cited

U.S. PATENT DOCUMENTS

| | | |
|---|---|---|
| 3,850,172 | 11/1974 | Cazalis . |
| 3,972,332 | 3/1976 | Wakim . |
| 4,485,490 | 12/1984 | Akers .................................... 128/846 |
| 4,553,967 | 11/1985 | Ferguson et al. . |
| 4,903,710 | 2/1990 | Jessamine ............................. 128/846 |
| 5,018,534 | 5/1991 | Grant . |
| 5,019,031 | 5/1991 | Towfighi et al. . |
| 5,020,546 | 6/1991 | Russo ..................................... 128/849 |
| 5,178,162 | 1/1993 | Bose . |
| 5,224,940 | 7/1993 | Dann et al. . |
| 5,248,307 | 9/1993 | Sokoloff . |
| 5,316,541 | 5/1994 | Fischer . |
| 5,339,834 | 8/1994 | Marcelli . |
| 5,396,904 | 3/1995 | Hartigan, Jr. . |
| 5,514,119 | 5/1996 | Curtis .................................... 128/760 |

*Primary Examiner*—Michael A. Brown
*Attorney, Agent, or Firm*—Zarley, McKee, Thomte, Voorhees, & Sease

[57] ABSTRACT

A metal basin includes a grid of metal rods for supporting a limb extremity above irrigation fluids collected in the bottom of the basin. A free standing, transparent plastic enclosure is removably attached to the basin through fasteners along the lower edge of the side walls of the enclosure. The disconnecting of fasteners along one side of the enclosure allows pivoting the enclosure off of the extremity. Hand access openings in the side walls of the enclosure accommodate hands and allow the extremity to extend into the enclosure chamber.

9 Claims, 3 Drawing Sheets

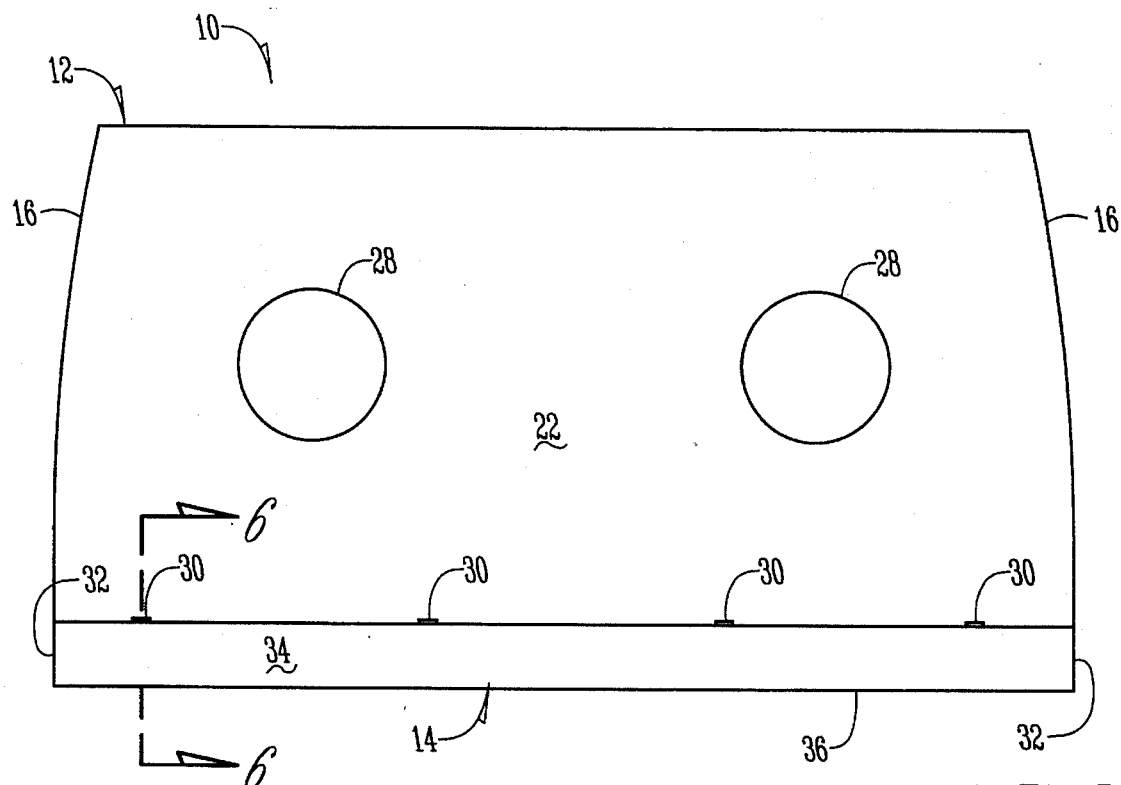
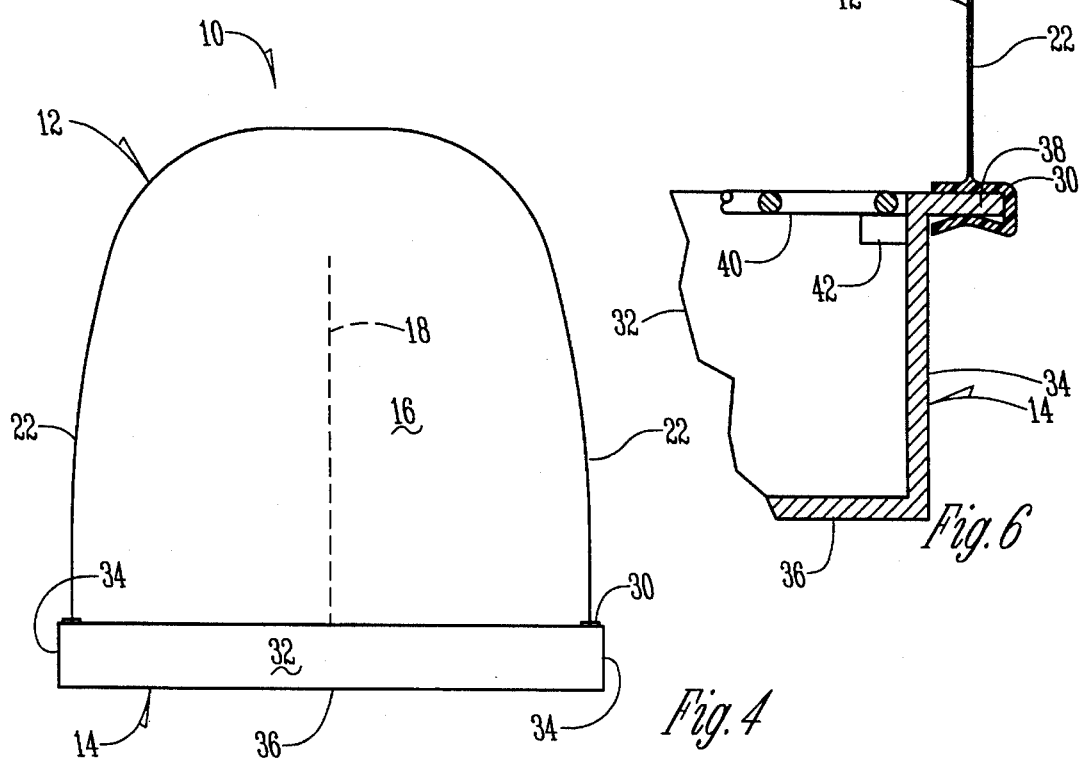
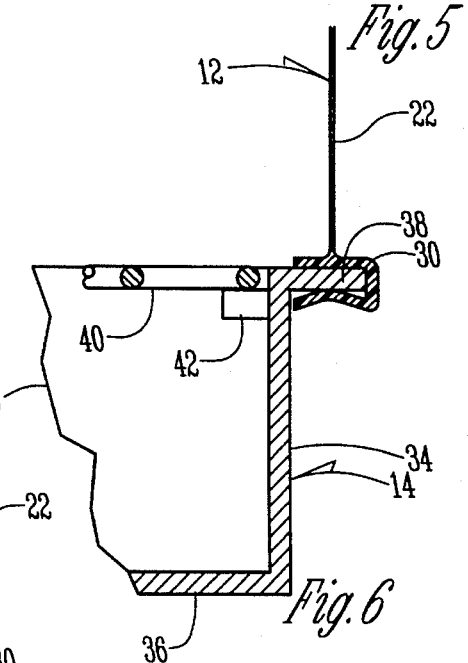
Fig. 5
Fig. 6
Fig. 4

SURGICAL SHIELD FOR ORTHOPEDIC SURGERY

BACKGROUND OF THE INVENTION

In performing orthopedic surgical procedures it is desirable to protect the surgeon and assistants from irrigant and other fluids while irrigating open wounds and fractures. Different enclosures have been provided for the limb extremity such as disclosed in the Fischer U.S. Pat. No. 5,316,541 (1994), and Bose U.S. Pat. No. 5,178,162 (1993). The Fischer enclosure is maintained erect by being inflated. The Bose enclosure is of a one piece, self contained construction, fabricated from a plastic material. In each case the extremity being worked upon remains in the fluids collected in the bottom of the enclosure.

What is needed is an orthopedic trauma basin with a shield that not only protects the surgeon and assistants, but also provides a dry work surface for supporting the limb extremity remote to the irrigation fluids in the basin.

SUMMARY OF THE INVENTION

A reusable, sterilizable metal basin includes a metal grid formed from metal rods supported in a spaced relation to the bottom of the basin for maintaining the limb extremity out of the irrigation fluids collected in the bottom of the basin. An outwardly extending peripheral flange extends around the top of the basin side wall and is engageable by a plurality of fasteners carried on the lower edge of a plastic throw-away enclosure. The enclosure includes hand openings on either side for the hands of the operating surgeon and assistants. A vertical slit is centered in the end walls of the enclosure, extending from the bottom edge upwardly to allow admission of the limb into the enclosure for being positioned on the grid.

The closure is fabricated from transparent plastic material which has sufficient inherent strength to free stand independent of any framework or other support. An acceptable material is polyethylene used for garbage bags. The thickness of the material will be determined by what is sufficient to allow the enclosure to free stand.

The side walls of the enclosure can include circular perforations which will allow side wall portions to be removed to provide circular access openings into the chamber of the enclosure. The end walls also include vertical slits which are formed by tearing serrations formed in the end walls.

The enclosure may be attached or removed from the basin easily by operating the fasteners removably attaching it to the outwardly extending flange around the basin exterior side wall. When the irrigation step of the operation is completed, the fasteners on one side of the enclosure can be removed and the enclosure then lifted off the limb and laid to one side of the basin, while still being connected to the basin on the one side. The enclosure is inexpensive to manufacture and thus can be a throw away item.

DESCRIPTION OF THE DRAWINGS

FIG. 5 is a side elevational view taken along the right side in FIG. 1.

FIG. 4 is an elevational end view thereof.

FIG. 6 is a cross-sectional view taken along line 6—6 in FIG. 5.

DESCRIPTION OF THE PREFERRED EMBODIMENT

Figure 1:
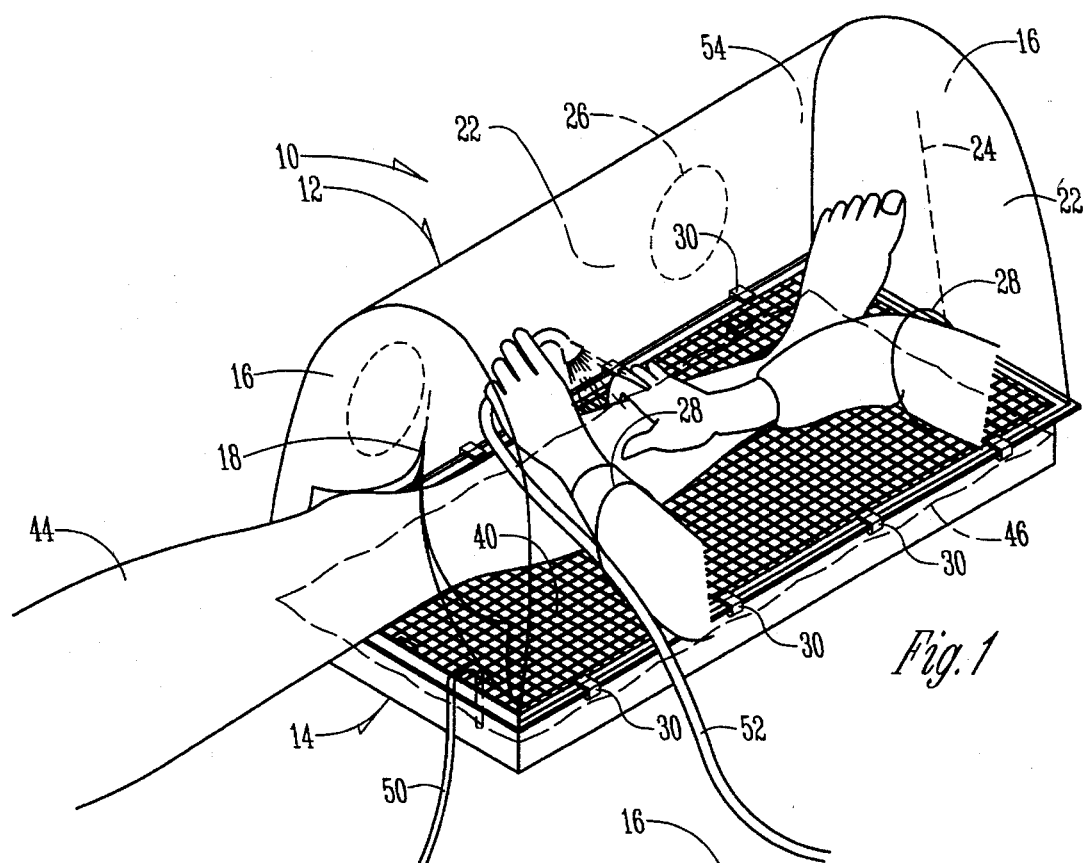
FIG. 1 is a perspective view of the trauma basin with shield of this invention, illustrating a limb extremity being operated on in the chamber under an enclosure shield.

A trauma basin with shield is referred to in FIG. 1 generally by the reference 10, and includes an enclosure shield of plastic material 12 detachably connected to a metal basin 14.

An enclosure shield 12 is fabricated from transparent plastic material such as polyethylene used in garbage bags but has a sufficient thickness to allow it to free stand independent of any other support, such as a framework. The enclosure 12 has opposite end walls 16 which include slits 18 extending upwardly from the lower edge 20 and centered between the opposite side walls 22. The slits may be formed by serrations 24 being torn open, as seen in FIG. 1. Circular serrations or perforations 26 are formed in the opposite side walls 22 to be torn away as needed to provide hand access openings 28. These openings would be on the order of 8 cm in diameter, leaving approximately 2 cm around a person's arm.

The lower edge 20 of the enclosure 12 includes integral plastic fasteners 30 for removably securing the enclosure to the basin 14 as hereinafter described.

The basin 14 includes opposite end walls 32, opposite side walls 34, and a bottom wall 36. The upstanding side walls 34 include a horizontally outwardly extending flange 38 to which the fasteners 30 are removably attached as seen in FIG. 6.

Figure 2:
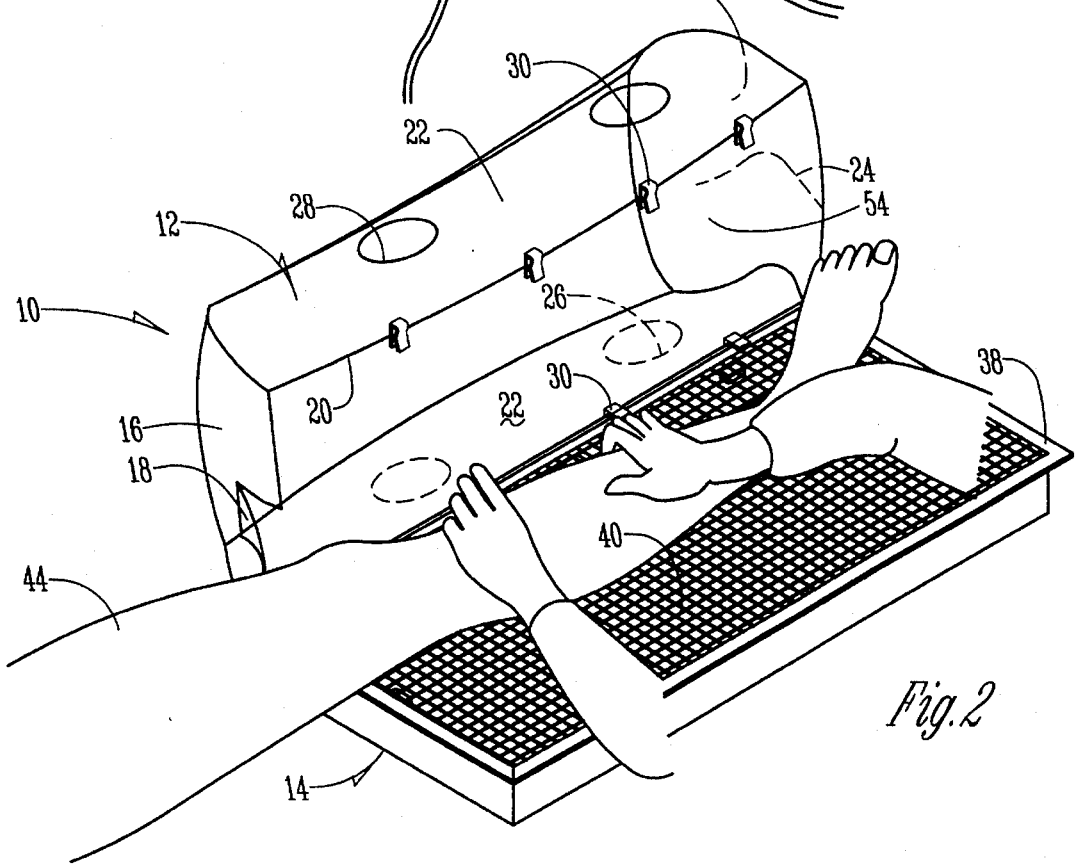
FIG. 2 is a view similar to FIG. 1 but showing the enclosure pivoted to an open position on one side of the basin.
Figure 3:
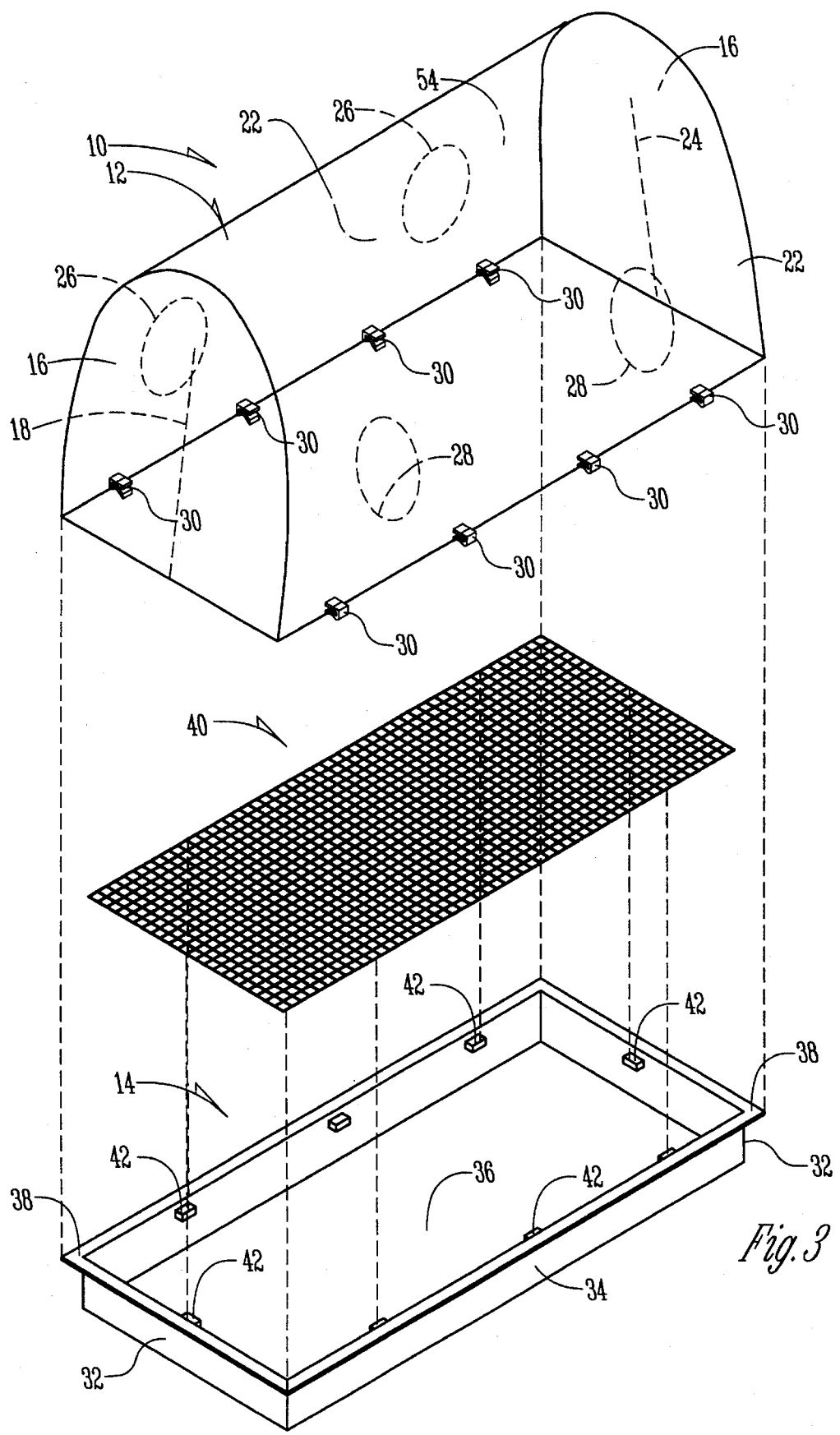
FIG. 3 is an exploded view of the basin, grill and enclosure.

A removable grid 40 is positioned in the basin 14 on ledge supports 42 such that the top surface of the grid 40 is coplanar with the top surface of the horizontal flange 38, thereby creating a smooth surface for supporting the limb extremity 44 as seen in FIG. 2. The grid is formed from 8 mm in diameter metal rods.

The height of the basin side walls 34 is approximately 4 cm, thus keeping the support grid 40 low, but yet above the irrigation liquid 46 as seen in the bottom of the basin 14 in FIG. 1. The grid includes uniform openings 2 cm×2 cm, which are large enough to receive a vacuum hose 50 and remove any items that might unintentionally fall through the grid openings. As also seen in FIG. 1, an irrigation hose 52 is positioned in the enclosure 54 to provide a fluid for cleaning the extremity 44. The hose 50 extends between the bottom edge 20 of the enclosure 12 and the basin side wall 34 into the grid 40 to the bottom wall 36 of the basin 14.

In use, the enclosure 12 would be fastened along one side to the basin 14 through use of the fasteners 30, engaging the flange 38 as seen in FIG. 2. The extremity 44 is then placed on the grid 40 and the enclosure is closed over the extremity 44 by fastening the remaining fasteners 30 to the flange 38 as seen in FIG. 1. Through use of the irrigation hose 52, cleaning of the extremity 44 is accomplished. Only those access openings 28 are created that are needed by the surgeon and assistants. Once the cleaning of the extremity 44 has been completed, the enclosure 12 may be pivoted to the open position as seen in FIG. 2 by releasing the fasteners 30 on one side only. It is seen that by the slits 18 extending upwardly from the bottom edge 20 of the enclosure end walls 16, the slits 18 custom fit around the extremity 44 and allow removal of the enclosure without the extremity being removed from the basin 14. If the extremity 44 extends through the enclosure 12 (not shown), slits 18 in both end walls will be used.

What is claimed is:

1. A surgical shield for use in limb surgery to isolate an extremity upon which surgery is to be performed, comprising a basin having a bottom wall and an upstanding peripheral wall, said peripheral wall having a horizontally extending flange, and said peripheral wall extending along opposite sides and opposite ends of said basin, an enclosure of transparent plastic material on said basin forming a chamber to receive an extremity, said enclosure having a bottom peripheral edge engaging said basin peripheral wall flange, fasteners removably securing said bottom peripheral edge of said enclosure to said peripheral wall flange of said basin, and a grid in said basin positioned on supports on the peripheral wall of said basin, said grid being in spaced relation to the bottom wall of said basin to allow said extremity to be positioned above irrigation liquids collected in said basin below said grid.

2. The surgical shield of claim 1 and said plastic material of said enclosure has properties which allow said enclosure to free stand independently of any other support.

3. The surgical shield of claim 1 wherein said fasteners are integral with the bottom peripheral edge of said enclosure.

4. The surgical shield of claim 1 wherein said peripheral wall horizontal flange extends outwardly.

5. The surgical shield of claim 1 wherein said enclosure includes hand access openings on opposite sides of said enclosure to give access to said chamber.

6. The surgical shield of claim 5 wherein said enclosure includes an end wall having a vertical slit centered between opposite side walls of said enclosure and extending upwardly from said bottom edge to allow for an extremity to extend into said chamber and on to said grid.

7. The surgical shield of claim 1 and said grid and horizontal flange on said basin have coplanar top surfaces.

8. The surgical shield of claim 1 wherein said grid has uniformly spaced apart openings approximately two centimeters by two centimeters.

9. The surgical shield of claim 8 and a vacuum hose is positioned under the bottom peripheral edge of said enclosure and on said basin wall and flange and extends through one of said grid openings to the bottom wall of said basin to remove irrigation liquid collected in said basin.

* * * * *